US008728111B2

(12) United States Patent
Geist et al.

(10) Patent No.: US 8,728,111 B2
(45) Date of Patent: May 20, 2014

(54) GUIDEWIRE AND METHOD FOR SURGICAL PROCEDURES

(71) Applicant: Safe Wire Holdings, LLC, Davie, FL (US)

(72) Inventors: Wyatt Drake Geist, Davie, FL (US); Arden Allen Geist, Sr., Indialantic, FL (US)

(73) Assignee: Safe Wire Holdings, LLC, Davie, FL (US)

( * ) Notice: Subject to any disclaimer, the term of this patent is extended or adjusted under 35 U.S.C. 154(b) by 0 days.

(21) Appl. No.: 13/973,677

(22) Filed: Aug. 22, 2013

(65) Prior Publication Data

US 2013/0338674 A1    Dec. 19, 2013

Related U.S. Application Data

(63) Continuation-in-part of application No. 13/722,667, filed on Dec. 20, 2012, now Pat. No. 8,540,676, which is a continuation-in-part of application No. 13/037,947, filed on Mar. 1, 2011, now Pat. No. 8,545,531, which is a continuation-in-part of application No. 12/823,791, filed on Jun. 25, 2010, now Pat. No. 8,361,102.

(60) Provisional application No. 61/220,828, filed on Jun. 26, 2009.

(51) Int. Cl.
  *A61M 29/00* (2006.01)
(52) U.S. Cl.
  USPC ......................................................... 606/198

(58) Field of Classification Search
  USPC ............. 604/164.01, 104, 106, 107; 606/313, 606/326–327, 198; 600/200, 434, 585, 567
  See application file for complete search history.

(56) References Cited

U.S. PATENT DOCUMENTS

| | | | |
|---|---|---|---|
| 4,654,028 A | 3/1987 | Suma | |
| 5,217,484 A | 6/1993 | Marks | |
| 5,431,651 A | 7/1995 | Goble | |
| 5,433,723 A | 7/1995 | Lindenberg et al. | |
| 5,509,919 A | 4/1996 | Young | |
| 5,653,716 A | 8/1997 | Malo et al. | |
| 5,795,308 A | 8/1998 | Russin | |
| 6,482,178 B1 * | 11/2002 | Andrews et al. | ......... 604/164.01 |
| 7,169,160 B1 | 1/2007 | Middleman et al. | |
| 7,367,975 B2 | 5/2008 | Malecki et al. | |
| 7,575,578 B2 | 8/2009 | Wetzler et al. | |
| 7,637,945 B2 | 12/2009 | Solem et al. | |
| 7,766,812 B2 | 8/2010 | Schroeder et al. | |
| 7,914,493 B2 | 3/2011 | Venbrux et al. | |
| 2005/0267555 A1 | 12/2005 | Marnfeldt et al. | |

(Continued)

*Primary Examiner* — Sameh Boles
(74) *Attorney, Agent, or Firm* — McHale & Slavin, P.A.

(57) ABSTRACT

A surgical guide wire or K-wire and method of use are provided. The K-wire, or guide wire, has opposite end portions and a shank portion in between. One end portion has a deformable end portion that, once outside of a confining guide passage, can be deformed to present a projected forward facing area that is larger than the transverse cross section of the K-wire, or guide wire, while in the passage. The increased area will provide increased resistance to additional forward axial movement into the surgical site.

13 Claims, 12 Drawing Sheets

(56) References Cited

U.S. PATENT DOCUMENTS

| | | |
|---|---|---|
| 2006/0064101 A1 | 3/2006 | Arramon |
| 2007/0191778 A1 | 8/2007 | Venbrux et al. |
| 2007/0239159 A1 | 10/2007 | Altarac et al. |
| 2007/0270896 A1 | 11/2007 | Perez-Cruet |
| 2008/0071223 A1 | 3/2008 | Stauber |
| 2009/0182245 A1 | 7/2009 | Zambelli |
| 2009/0275946 A1 | 11/2009 | Duncan |
| 2013/0110118 A1 | 5/2013 | Geist et al. |

\* cited by examiner

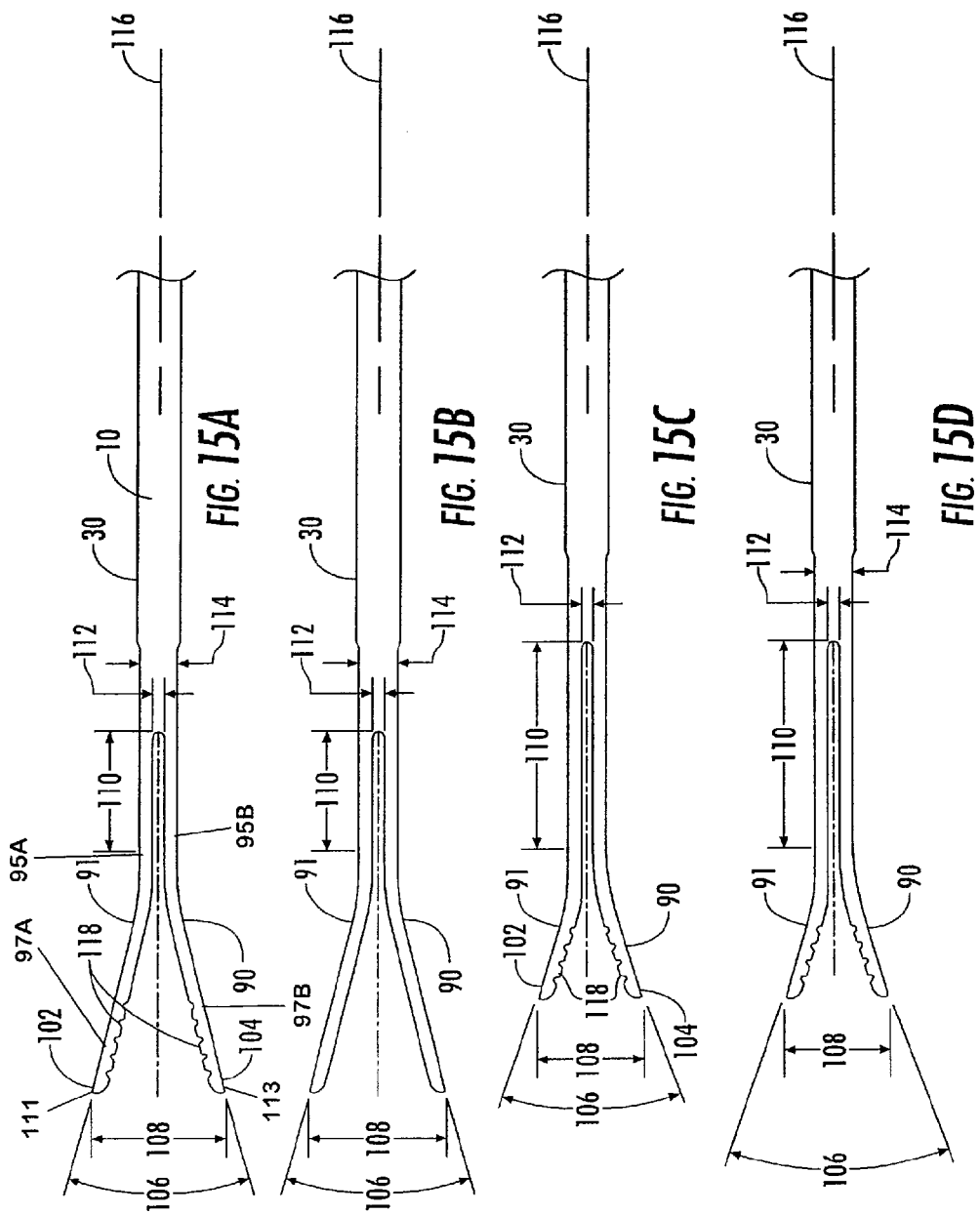

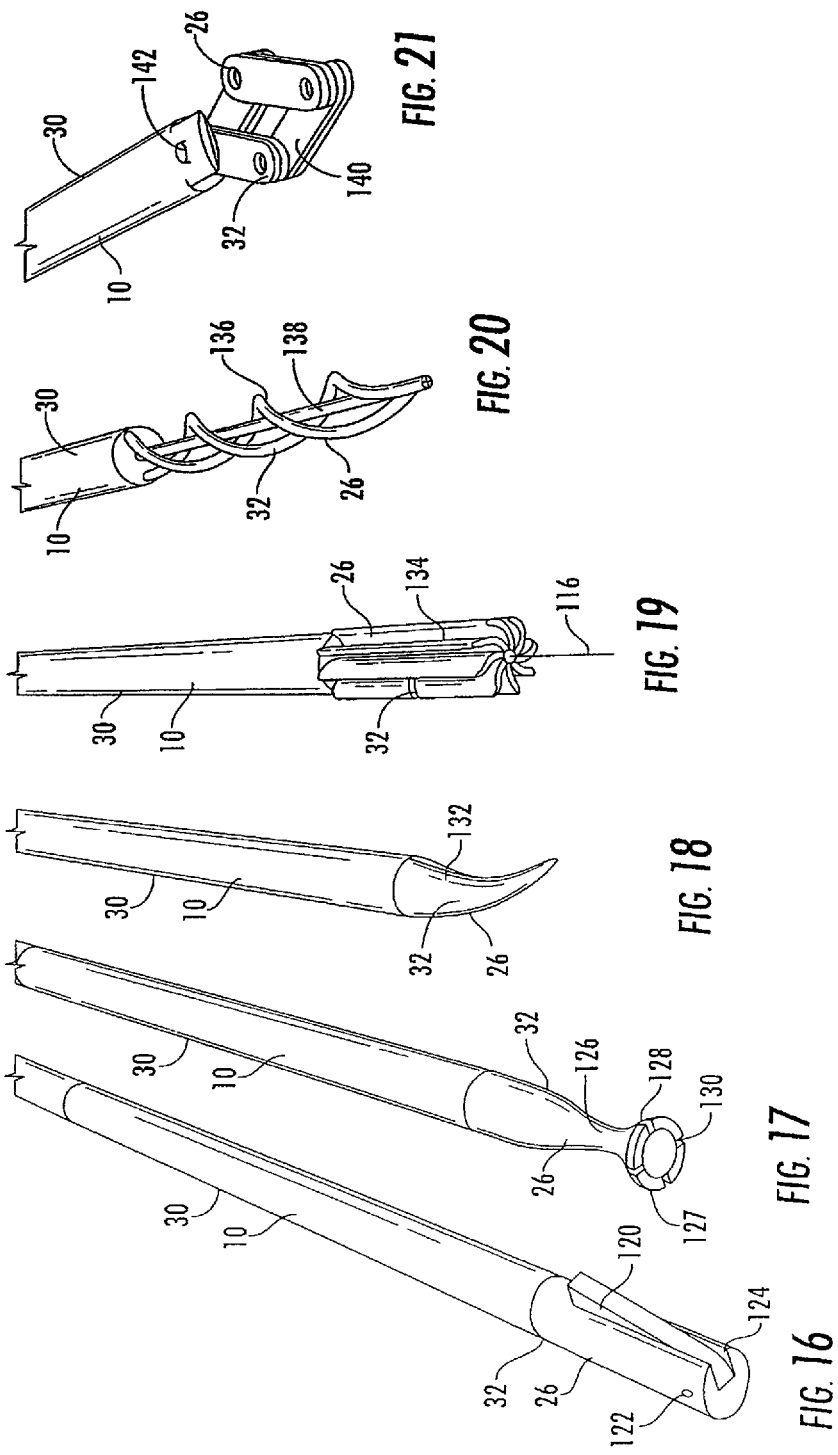

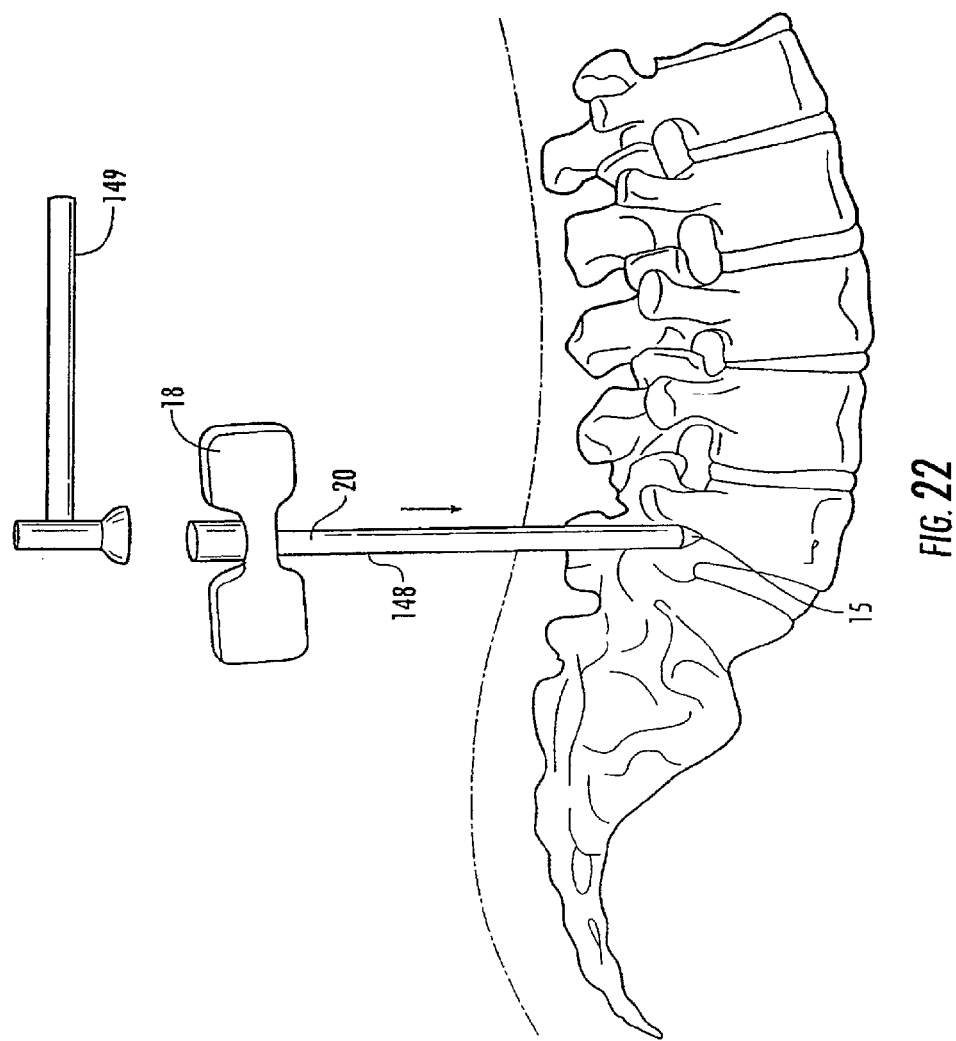

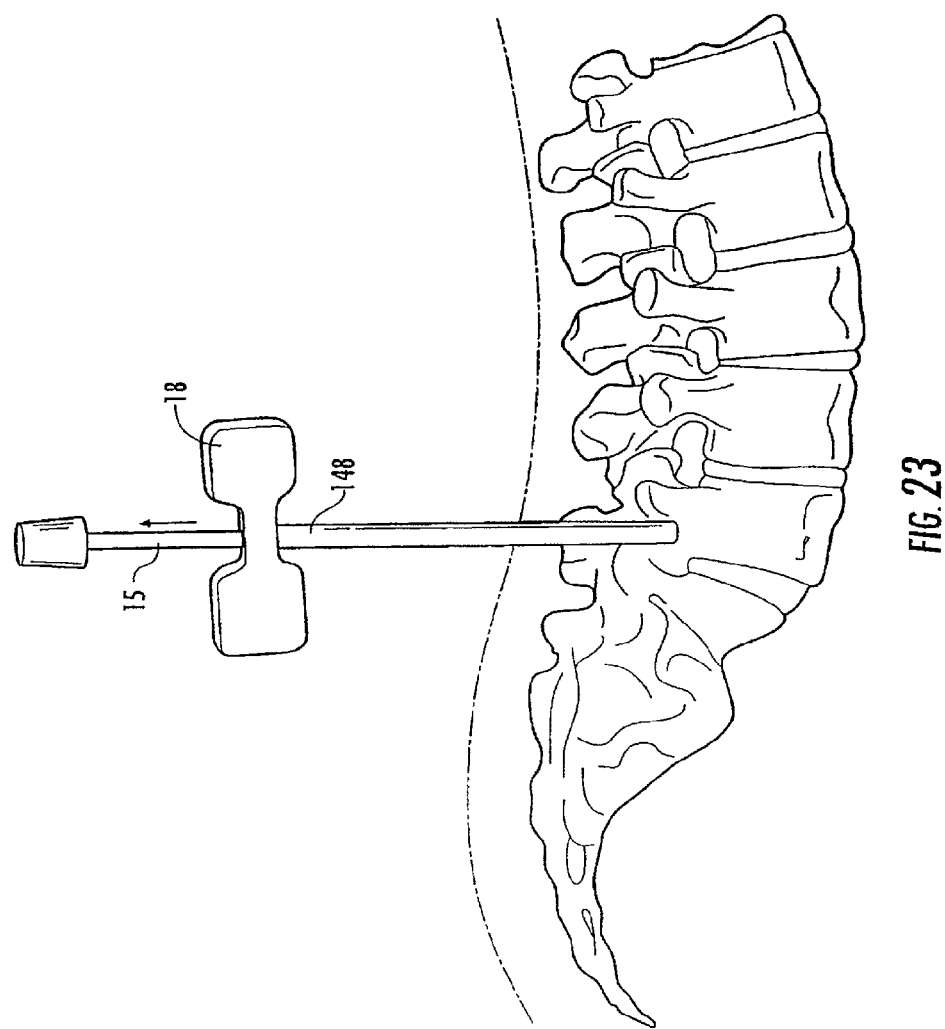

GUIDEWIRE AND METHOD FOR SURGICAL PROCEDURES

CROSS REFERENCE TO RELATED APPLICATIONS

In accordance with 37 C.F.R 1.76, a claim of priority is included in an Application Data Sheet filed concurrently herewith. Accordingly, under 35 U.S.C. §119(e), 120, 121, and/or 365(c) the present invention claims priority as a continuation-in-part to U.S. Non-Provisional application Ser. No. 13/722,667; filed Dec. 20, 2012, entitled, "GUIDEWIRE AND METHOD FOR SURGICAL PROCEDURES", which is a continuation-in-part to U.S. Non-Provisional application Ser. No. 13/037,947, filed Mar. 1, 2011, entitled, "GUIDEWIRE AND METHOD FOR SURGICAL PROCEDURES", which is a continuation-in-part of U.S. Non-Provisional Utility application Ser. No. 12/823,791, filed Jun. 25, 2010, entitled, "K-WIRE AND METHOD FOR SURGICAL PROCEDURES", which claims priority to U.S. Provisional Application No. 61/220,828, filed Jun. 26, 2009, entitled, "K-WIRE AND METHOD FOR SURGICAL PROCEDURES". The contents of each of the above referenced applications are herein incorporated by reference in its entirety.

FIELD OF INVENTION

The present invention relates to an improved guide wire or K-wire for use in surgical procedures such as orthopedic procedures; and in particular, to spinal procedures such as percutaneous pedicle screw constructs.

BACKGROUND OF THE INVENTION

In certain surgical procedures, a K-wire (Kirschner wire) or guide wire is used in combination with a surgical tool, such as a jamshidi needle. The jamshidi needle is generally used to form a hole through bone as a first step in certain medical procedures, such as attaching a screw to a pedicle. The K-wire, or guide wire, is inserted through the cannula of the jamshidi sheath into the interior of the bone. This procedure, if not completed properly can injure the patient, particularly if it engages certain sensitive parts which may include breaching the anterior cortex of a vertebral body. The K-wire, or guide wire, is used as a portal for certain surgical steps like guiding a drill, tap, screw, screwdriver or the like to the surgical site. The procedures oftentimes require the use of force which can cause a properly positioned K-wire, or guide wire, to move forward into or through the surgical site; which, if excessive, can move into contact where contact is to be avoided.

A K-wire, or guide wire, includes a generally elongated cylindrical shape and has a preferred diameter of about 1.3 millimeters, although the diameter can vary depending on the procedure and hardware being utilized for the procedure.

The cross sectional size and shape of the K-wire is limited only by the tools and devices it is used with. Each tool or device is typically provided with a through bore for receiving the K-wire, or guide wire, limiting the size and type of wire that can be used. Additionally, the K-wire is typically removed by passage through a through bore in a device or tool. Thus, to date, only K-wires with a small diameter, generally cylindrical round cross section, have been used; which presents the problem in their use. The relatively small diameter, combined with a lack of impeded movement, allows movement during a surgical procedure. Such movement is often difficult to notice during a surgical procedure where vision is limited by fluids, tissue and/or bone, and may further require x-rays or the like to determine the position of the wire. It should also be noted that while the K-wires, or guide wires, illustrated herein include a solid center core, the K-wire, or guide wire, may be a hollow tubular member without departing from the scope of the invention.

The present invention provides various solutions to this problem by providing an improved K-wire, or guide wire, which, when inserted, provides increased resistance to forward axial movement while still being usable with traditional surgical tools and devices.

The present invention also provides easy removal of the K-wire, or guide wire, through traditional surgical tools and devices.

DESCRIPTION OF THE PRIOR ART

U.S. Pat. No. 5,431,651 discloses a cross pin and set screw femoral and tibial fixation device for mounting a ligament graft. The device includes a drill guide for drilling a transverse hole. The drill guide is releasable from a first twist drill so as to leave it in place. The first twist drill is used to guide further drilling and passage of a fastener device. A K-wire or the first twist drill is used for guiding a second twist drill for enlarging the transverse hole and for guiding and turning a cannulated fastener device into a femoral bone end of the ligament graft. There is no feature on the K-wire to limit the extent of its insertion subsequent to it passing through the bone.

U.S. Pat. No. 7,575,578 discloses a surgical drill guide including a handle and an arm having an end which contacts a bone. The handle includes a plurality of slots or channels which receive a sleeve. The sleeve is used to guide a K-wire into the bone. The K-wire serves as a guide for drilling a tunnel into the bone. The K-wire does not include a feature to limit the extent of its insertion subsequent to it passing through the bone.

U.S. Published Patent Application No. 2007/0239159 discloses devices and systems for placing bone stabilization components in an individual. In particular, the bone stabilization components are placed on the spine. Various tools, including a K-wire, are employed to properly locate, place and secure the devices in an individual.

U.S. Published Patent Application No. 2007/0270896 discloses a device for accessing the pedicle of a vertebra including a Jamshidi needle.

SUMMARY

The present invention involves the provision of a K-wire which can be used with traditional surgical tools and devices. The inventive guide wire or K-wire has an end portion that, upon exit from the through bore of a surgical tool or device, can be changed in a controlled manner to present a deformable end portion that will provide a forward face with a larger projected area than the end surface of the K-wire while in the through bore. The deformation may be induced mechanically, from internal stress, thermally or otherwise.

The present invention also involves the provision of a method of conducting surgery utilizing a guide wire, or K-wire. The method includes passing a guide wire or K-wire through a tool or device into a surgical opening with the guide wire, or K-wire, presenting a forward facing area of a first size. The guide wire, or K-wire, then has an end portion, when moved out of the tool or device, where the forward end portion can be expanded to present a forward facing area of a second size larger than the first size. After use, the guide wire or K-wire may be extracted from the surgical site through a surgical tool or device.

BRIEF DESCRIPTION OF THE DRAWINGS

FIG. 15A is an enlarged side view of one embodiment of the present invention;

FIG. 15B is an enlarged side view of one embodiment of the present invention;

FIG. 15C is an enlarged side view of one embodiment of the present invention;

FIG. 15D is an enlarged side view of one embodiment of the present invention;

FIG. 16 is an enlarged perspective view of one embodiment of the present invention;

FIG. 17 is an enlarged perspective view of one embodiment of the present invention;

FIG. 18 is an enlarged perspective view of one embodiment of the present invention;

FIG. 19 is an enlarged perspective view of one embodiment of the present invention;

FIG. 20 is an enlarged perspective view of one embodiment of the present invention;

FIG. 21 is an enlarged perspective view of one embodiment of the present invention;

FIG. 22 is a partial side view illustrating insertion of a Jamshidi needle into the pedicle of a human spine;

FIG. 23 is a partial side view illustrating the removal of the needle from within the jamshidi, leaving the cannulated portion in place within the bone;

Like numbers used throughout the figures designate like or similar parts and/or construction.

DETAILED DESCRIPTION OF THE INVENTION

Figure 1:
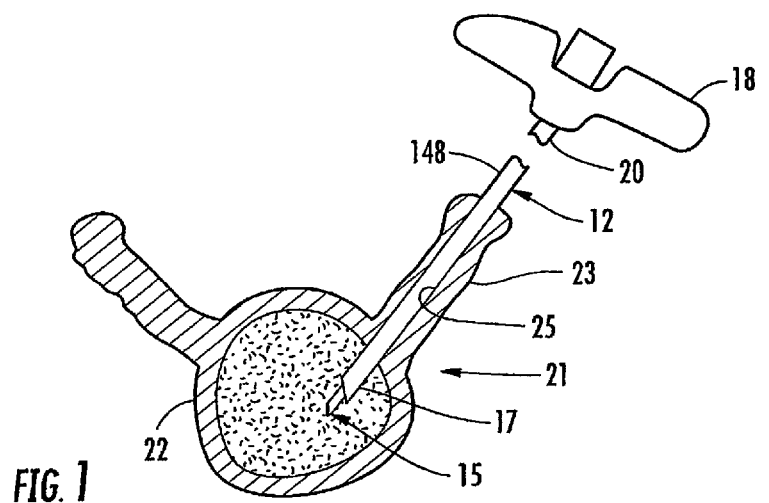
FIG. 1 is a schematic plan view of vertebra showing a jamshidi needle extending through a pedicle.

While the present invention is susceptible of embodiment in various forms, there is shown in the drawings and will hereinafter be described presently preferred embodiments with the understanding that the present disclosure is to be considered an exemplification of the invention and is not intended to limit the invention to the specific embodiments illustrated.

Referring generally to the figures, the reference numeral 10 designates generally a K-wire, or guide wire, usable in surgical procedures in combination with a surgical tool such as a jamshidi needle 12, drill or tap (not shown), or a surgical device such as a screw, plate or implant. K-wires (also called Kirschner wires or guide wires) are well known in the art. Jamshidi needles are also well known in the art, and have a tubular member 148 with a through bore 16 (as would a drill, tap or screw) and a removable and replaceable rod member 15 having a sharpened distal end 17. The rod member 15 is held in place within the through bore by threads or a bayonet mount (not shown) as is known in the art. A handle 18 may also be provided at the proximal end 20 of the tubular member 148 for facilitating insertion of the tubular member into a surgical site 21, such as a vertebra 22 with a pedicle 23 in a patient such as a human. A surgeon may manipulate the jamshidi needle 12 using the handle 18, and may also apply impact force to the tubular member 148 by striking the handle 18 with a hand or impact tool such as a hammer 149, as illustrated in FIG. 22. Jamshidi needles are used to penetrate bone in the performance of a surgical procedure such as attaching a screw 24 (FIG. 5B) to bone. A rod 15 may be installed in the through bore 16 during hole formation to increase rigidity of the tubular member 148. The rod 15 is removed to provide a through bore 16 for the K-wire 10 insertion. After forming a hole 25 with the jamshidi needle 12, the K-wire, or guide wire 10, is inserted into the interior of the bone and the jamshidi needle is removed, leaving the K-wire, or guide wire, in place within the bone. In some surgical procedures, like spinal surgery, the K-wire, or guide wire, is inserted through one wall of a bone, e.g., a pedicle 23, and is placed against an opposite bone wall. If care is not taken during surgery, the K-wire, or guide wire, may be pushed through the opposing bone wall creating a risk of injury. The present invention is a solution to this potential problem.

The K-wire, or guide wire 10, is typically used as a pilot or guide for other surgical tools or devices such as drills, taps, plates, implants and screws. In the attachment of a screw 24 (FIG. 5B), the screw can have a through bore 44 that receives the K-wire, or guide wire, for guiding the screw to a hole 25 that was formed with the jamshidi and thereafter drilled and tapped using the K-wire, or guide wire as a guide. After installation of the screw 24, the K-wire, or guide wire 10, is then extracted through the through bore 44 of the screw 24 by simply pulling on the K-wire, or guide wire, to reduce the frontal area of the K-wire, or guide wire, substantially to its original size.

The K-wire, or guide wire 10, has opposite end portions 26, 28 and a generally cylindrical intermediate portion 30 positioned between the end portions. The length of the K-wire, or guide wire 10, is preferably long enough to extend beyond both ends of the surgical tool being used, e.g., a jamshidi needle 12. The K-wire, or guide wire 10, is sized and shaped to be freely movable along the through bore 16. The end portion 28 will be referred to as the manipulative end, and the end portion 26 will be referred to as the operative end for convenience. Preferably, the entire length of the manipulative end portion 28 and the intermediate portion 30 is generally cylindrical to facilitate removal of a tool or device from an installed K-wire, or guide wire 10.

The operative end portion 26 is provided with a section 32 that is controllably deformable. The section 32 may be an integral portion of the K-wire, or guide wire 10, or attached thereto. Several different sections 32 are described below. In general, the section 32 is configurable to fit within the through bore 16 and be freely movable therein. The K-wire, or guide wire, is insertable into the through bore 16 for insertion into the surgical site 21 for use and for removal from a through bore in the tool or device. The K-wire, or guide wire, may also be removed prior to a later surgical step if it is no longer needed. For example, if the K-wire, or guide wire, is not needed to guide the screw 24 for insertion, it may be removed prior to attaching the screw 24. When outside of the through bore 16, the operative end 26 expands automatically or can be manually expanded to present an expanded face with a projected area greater than the transverse cross sectional area of the K-wire, or guide wire 10, while positioned in the through bore 16. By way of example, the operative end 26 seen in FIG. 3 has a projected area of approximately (given that the end 33 of the bend at the intermediate section 30 of K-wire, or guide wire 10, is rounded reducing the area slightly) L times W whereas the K-wire, or guide wire, has a cross sectional area of $A=\pi r^2$ where r is equal to W/2. It is preferred that the reconfigured cross sectional projected area be at least about 1.5 times, and preferably at least about twice the size of the first cross sectional area of the K-wire, or guide wire, as described below.

Figure 2A:
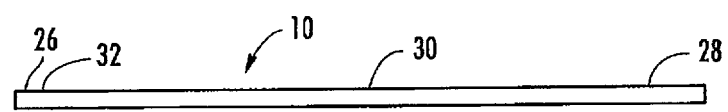
FIG. 2A is a side elevation view of a typical prior art K-wire, or guide wire, having a straight cylindrical body and forward face.
Figure 2B:
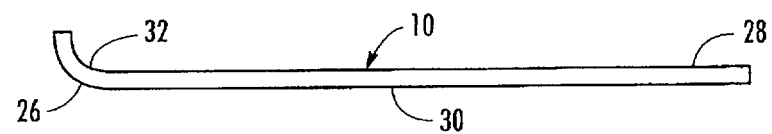
FIG. 2B is a side elevation view of one embodiment of a K-wire, or guide wire, of the instant invention showing an end configuration that curls to create an enlarged end face to resist forward migration.
Figure 5A:
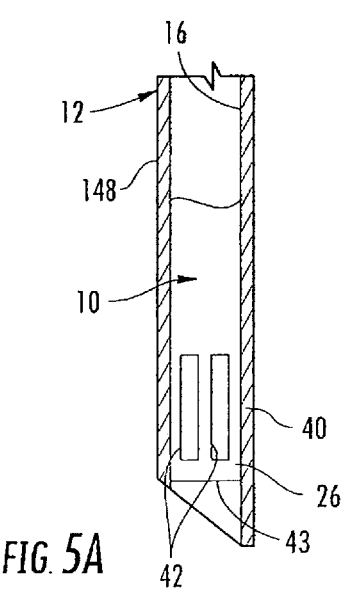
FIGS. 5A and 5B are enlarged fragmentary side views of one embodiment having a reformable end portion.
Figure 5B:
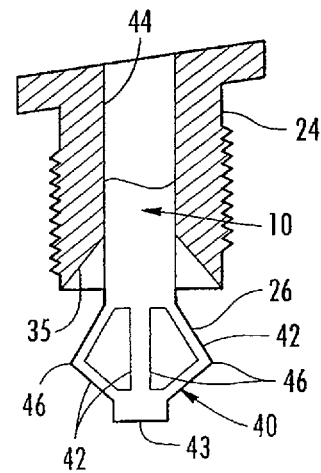

The K-wire, or guide wire 10, or the deformable portion 32 of the K-wire, or guide wire, may be made of a deformable material which will allow at least the operative end 26 to be configured between first and second configurations (see FIGS. 2A and 2B) with one configuration (FIG. 2B) presenting a larger projected area than the first (FIG. 2A) as discussed above. One suitable reconfigurable material is referred to as a shape memory alloy such as Nitinol. A reversible, solid phase transformation known as martensitic transformation is the force behind shape memory alloys. Such alloys are well known and form a crystal structure, which is capable of undergoing a change from one form of crystal structure to another. Temperature change and/or loading can initiate the shape transformation. By way of example, above its transformation temperature, Nitinol is superelastic, able to withstand deformation when a load is applied and return to its original shape when the load is removed. Below its transformation temperature, it displays the shape memory effect. When it is deformed below its transformation temperature, it will remain in that shape until heated above its transformation temperature, at which time it will return to its original shape. The original shape would then be the bent form, and then it can be reformed cold to straight. Upon heating, the bend will return. The heat (or temperature increase) can be provided by contact with the patient. Elastically deformable materials may also be used, such as spring steel with high yield strength where stress is induced to change a shape that is elastically released to change the shape of the deformed member back to its non stressed shape. An embodiment of the invention is shown in FIGS. 5A and 5B that could be made using a spring material and is described below. Plastically deformable materials might also be used for some operative end portion 26 configurations. The terms resiliently deformable, plastically deformable and spring are used generally to indicate a material property when the material is deformed during typical use of the K-wire, or guide wire, as described herein. Controlled bending can be induced by using controlled weak points, such as a groove or the like, at selected strategic locations. The embodiment in FIGS. 5A and 5B might also be used with a plastically deformable material. The screw 24 or other tool or device that is anticipated to be the last one used with the K-wire, or guide wire 10, may be provided with a forcing cone 35 to help reconfigure the end portion 26 back to its unexpanded shape to conform it to fit within a passage like passages 16, 44 for insertion or removal. An embodiment of this form is seen in FIGS. 5A and 5B and is described below.

Figure 3:
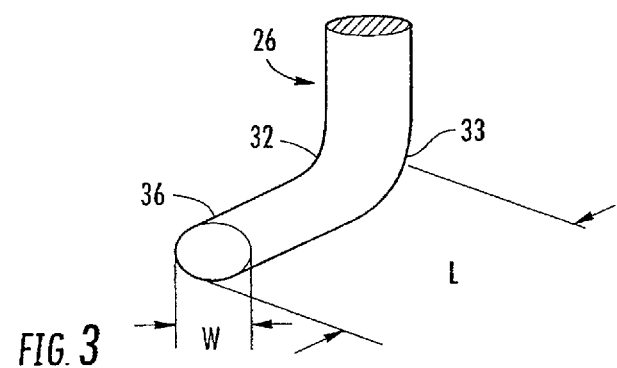
FIG. 3 is an enlarged fragmentary view of a K-wire, or guide wire, showing an end portion configured to present an expanded forward face.

In the embodiment shown in FIGS. 1-3, the operative end 26 has a laterally extending portion 36 when out of the through bore 16. The deformation to lateral extension may be provided as described above by applying heat to effect bending from memory. The portion 36 may be provided as a permanent bend in the K-wire, or guide wire 10, which can then be deformed to straight by confinement in the through bore 16, and upon exit from the through bore will reassume its bent configuration. The material properties of the end portion 26 may be selected to provide for straightening of the bend for removal through a passage or bore which may be facilitated, e.g., by the use of a forcing cone 35. The lateral extension presents a larger projected area to further limit forward axial motion into the surgical site.

Figure 4:
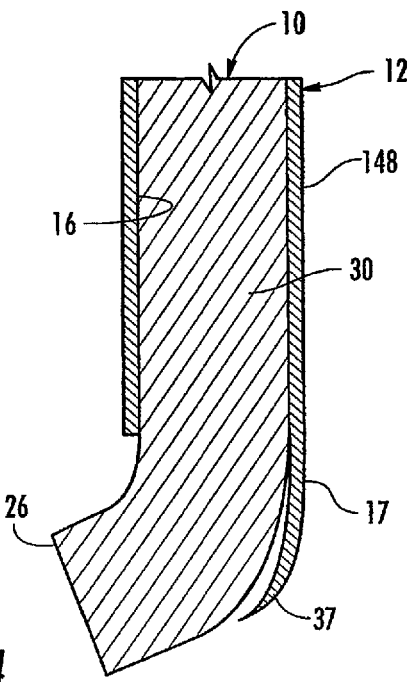
FIG. 4 is a fragmentary side sectional view of a jamshidi needle with a K-wire, or guide wire, emerging from a through bore.

FIG. 4 shows a surgical tool configuration that can be used to facilitate directing a K-wire, or guide wire 10, out of the through bore 16. It uses a curved tip 37 to direct the exiting K-wire, or guide wire 10.

In the embodiment shown in FIGS. 5A and 5B, the operative end 26 is in the form of an expandable cage 40 having a plurality of rods 42 that can assume an expanded position. FIG. 5A illustrates a contracted configuration of cage 40 when in a through bore 16 of tubular member 148. FIG. 5B illustrates the cage 40 in its expanded configuration and a screw positioned on the K-wire, or guide wire 10. The embodiment of FIGS. 5A and 5B may be constructed in at least two ways, resiliently deformable rods 42 or plastically deformable rods 42. A memory metal alloy may be used. A polymeric material such as PEEK or the like may also be used for at least the rods 42. If the rods 42 are elastically deformable, they can be formed as biased to an outward or expanded configuration, where once outside of the through bore 16 they will move outwardly to relieve induced stress to provide the expanded configuration like in FIG. 5B. The rods 42 may also be plastically deformable, and upon application of axial force will move to an expanded position as in FIG. 5B. When the K-wire, or guide wire, is in the through bore 16, the rods 42 assume, or are in the contracted configuration; and when the rods 42 are outside of the bore, they assume or are forced into the expanded position, providing an increased projected area for engagement with material in the surgical site as discussed above. It is to be noted that the rods may also be made of a memory alloy as described above. The forcing cone 35 may be used to facilitate removal of the K-wire, or guide wire 10, through the through bore 44. The distal ends of the rods 42 may be held in place with an end cap 43. The projected area of the end portion 26 when expanded, as seen in FIG. 5B, would be that area defined or bounded by outermost extending portions of the rods 42 as at portions 46.

Figure 6B:
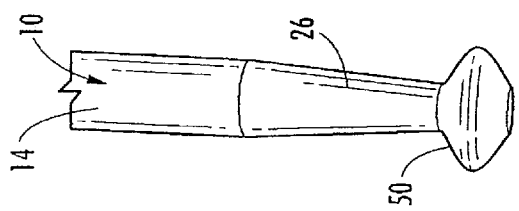
FIGS. 6A and 6B are enlarged side views of an end portion, expanded and unexpanded, of a further embodiment of a K-wire, or guide wire, of the present invention.
Figure 6A:
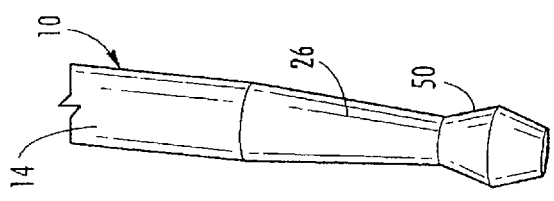

FIGS. 6A and 6B illustrate another embodiment of the invention. FIG. 6A shows an end portion 26 with an expandable end bulb 50 that may be made out of a memory alloy, which upon heating assumes the expanded configuration illustrated in FIG. 6B. This embodiment is particularly adapted for use when extraction of the K-wire, or guide wire, is other than through a tool or device passage.

Figure 7:
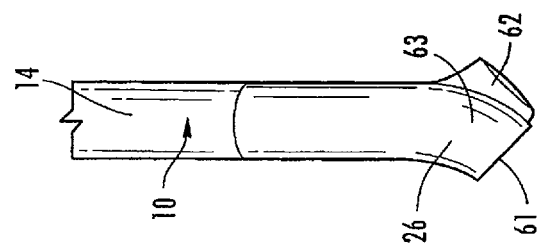
FIG. 7 is an enlarged side view of an end portion of a still further embodiment of a K-wire, or guide wire, of the present invention.

FIG. 7 illustrates another embodiment of the invention. It utilizes a pair of opposed legs 61, 62. The legs 61, 62 are constructed to move in an outward direction, either from spring action or from otherwise reassuming a formed shape, as from a spring type material or a temperature change as by using a memory alloy as described above. In the illustrated embodiment, the legs 61, 62 have overlying portions at 63.

Figure 8:
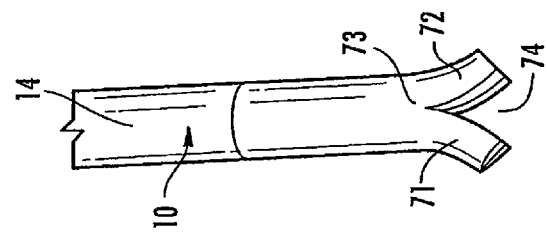
FIG. 8 is an enlarged side view of an end portion of a still further embodiment of a K-wire, or guide wire, of the present invention.

FIG. 8 illustrates an additional embodiment of the invention and is similar to the form shown in FIG. 7 by having two legs 71, 72, but the legs do not overlap; rather, the legs diverge from a common area 73 and have a gap 74 therebetween when in the extended position as shown.

The embodiments of the invention shown in FIGS. 6-8 may utilize a shank 14 of one material and an end portion of another material such as a spring material, a memory alloy or a polymeric material.

Figure 9:
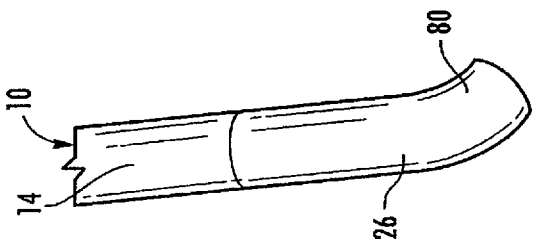
FIG. 9 is an enlarged side view of an end portion of an embodiment of the present invention similar to that shown in FIG. 2B.

FIG. 9 illustrates a still further embodiment of the present invention. It is similar to the K-wire, or guide wire 10, shown in FIGS. 2A and 2B and has a shank 14 with an attached end portion 26 having a single extending free end portion 80 shown in its extended configuration. The free end 80 may be provided as a permanent bend in the K-wire, or guide wire 10, which can then be deformed to straight by confinement in the through bore 16, and upon exit from the passage will reassume its bent configuration. The material properties of the free end portion 80 may be selected to provide for straightening of the bend for removal through a passage which may be facilitated, e.g., by the use of a forcing cone. The lateral extension of the free end presents a larger projected area to further limit forward axial motion into the surgical site.

Figure 10:
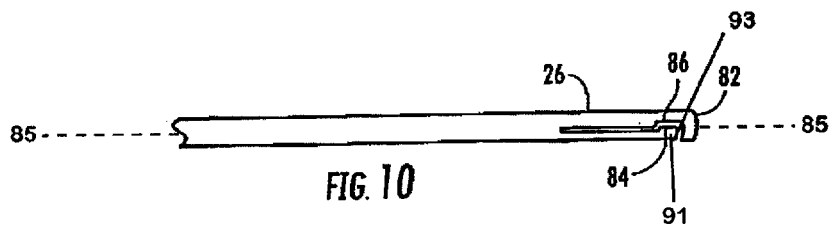
FIG. 10 is an enlarged side view of an end portion of one embodiment of the present invention.
Figure 11:
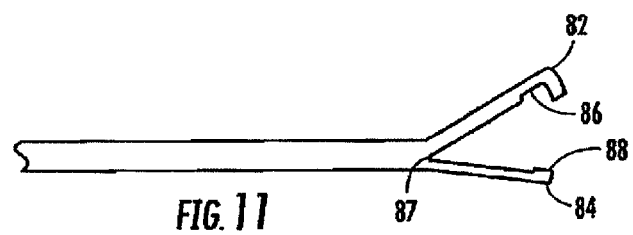
FIG. 11 is an enlarged side view of the embodiment illustrated in FIG. 10 with the end portions spread apart.

FIGS. 10 and 11 illustrate a still further embodiment of the present invention. The end portion 26 of the K-wire or guide wire includes a plurality of deformable ends, illustrated herein as independent legs 82 and 84. The K-wire or guide wire of FIGS. 10 and 11 can be made from a shape memory alloy such as Nitinol. Other shape memory alloys and materials can also be used. The ends 82 and 84 are normally deformed outwardly from the longitudinal axis 85 of the K-wire or guide wire at a common area diverging point 87 as shown in FIG. 11 within the guide wire. As such, the deformable ends, or legs 82 and 84 form separate structures which can move outwardly, independent of each other from the common area diverging point 87. The legs 82 and 84 are separated by a gap 87 which runs the length of the legs 82 and 84 and is orientated in a generally parallel manner from the longitudinal axis 85 of the guide wire 10. The deflection of the ends 82 and 84 presents a larger end surface area when the K-wire or guide wire is penetrating a bone. This larger end surface offers more resistance and consequently prevents the K-wire or guide wire from penetrating too far into the bone and perhaps passing into an adjacent bone or outside of the intended bone. The length of the ends 82 and 84 together with the different shape memory alloys determine how quickly the ends 82 and 84 deform outwardly after they enter a bone. The more rapidly they deform, the less they penetrate into a bone. The ends 82 and 84 collapse together, as shown in FIG. 10, when the K-wire or guide wire is withdrawn back through the Jamshidi needle. A groove 86 on end 82 permits projection 88 to fit therein when in the collapsed position.

As further illustrated, the K-wire or guide wire 10 is shown with one of the deformable ends being longer than the opposing deformable end. As illustrated, leg 82 is longer than leg 84. Leg 82 includes a tip portion 89 that extends past and is bent inwardly towards the leg 84 to overlap a tip portion 91 of the shorter leg 84. While most of the leg 82 is orientated in a generally parallel manner relative to the leg 84, at least a segment of, if not all of the tip portion 89 is positioned in a perpendicular orientation relative to the leg 84. A second gap 93 separates the tip portions 89 and 91. The second gap 93 therefore is formed substantially perpendicular to the longitudinal axis 85 when legs 82 and 84 are in the non-deployed or not separated state.

Figure 12:
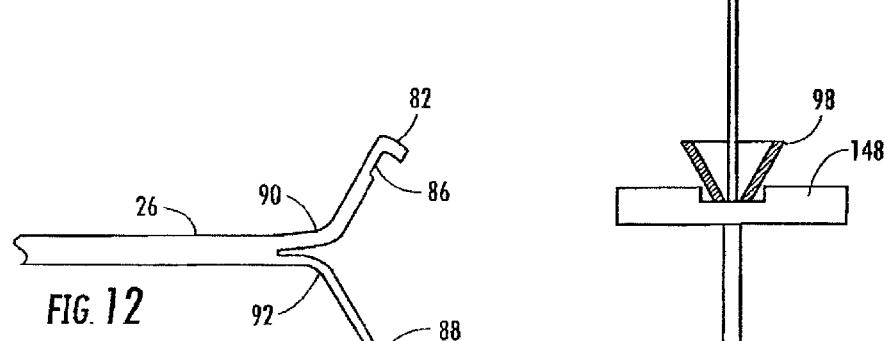
FIG. 12 is an enlarged side view of one embodiment of the present invention.
Figure 13:
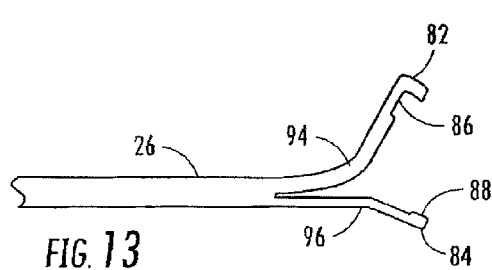
FIG. 13 is an enlarged side view of one embodiment of the present invention.

FIGS. 12 and 13 illustrate other embodiments of the present invention. These embodiments are variations of the embodiment illustrated in FIGS. 10 and 11. In FIG. 12 the end 82 of the K-wire or guide wire bends outwardly at 90. Also, end 84 bends outwardly at 92. The bends 90 and 92 are positioned within the legs 82 and 84 at some distance away from the common area diverging point 87, i.e. towards the tip portions 89 and 91. This embodiment permits the ends 82 and 84 to bend outwardly from the longitudinal axis more rapidly than the embodiments of FIGS. 10 and 11. In FIG. 13, the end 82 bends outwardly at 94 and the end 84 bends outwardly at 96. Bends 94 and 96 are closer to the tip portions 89 and 91. Thus, they permit the ends 82 and 84 to bend outwardly from the longitudinal axis more rapidly than the bends 90 and 92 of FIG. 12. The faster the ends move away from the longitudinal axis, the less the K-wire or guide wire penetrates into the bone. Therefore, the embodiment of FIG. 13 would penetrate less into a bone than the embodiment of FIG. 12. Also the embodiment of FIG. 12 would penetrate less into a bone than the embodiment of FIGS. 10 and 11.

FIGS. 15A-15D illustrate other embodiments of the present invention. These embodiments are variations of the embodiment illustrated in FIGS. 10 through 14. These embodiments generally include variations in the length of the free ends 102, 104, as well as variations in the location and type of bend that cause the free ends to bend outwardly. These variations, as well as variations in the diameter of the wire, permit significant control over the deployment of the device, e.g. increase in frontal area, as well as the devices engagement to the surrounding bone. The faster the ends move away from the longitudinal axis 116, the less the K-wire, or guide wire, penetrates into the bone and the more difficult it is to force the device forward with respect to its original deployed position. In FIGS. 15A-15D the ends 102 and 104 of the K-wire, or guide wire 10, bend outwardly at radii 90 and 91 respectively. The bend divides each free end 102, 104 into a first liner portion 95A, 95B and a second portion 97A, 97B. The second portions 97A, 97B diverge away from the longitudinal axis 116 at the bend when in the deployed state. The radii 90, 91 of the preferred embodiment are about 12 millimeters (mm). However, it should be noted that the radii can vary between 0 mm and about 200 mm without departing from the scope of the invention. In the non-limiting embodiments illustrated in FIGS. 15A and 15B, the free ends 102, 104 are bent to an included separation angle 106 of about 30 degrees, causing a frontal width 108 of about 4.7 mm in an unloaded condition. Additionally, a free length 110 of the ends is provided behind the bends 90 and 91 to allow additional flexibility to the free ends. In the preferred embodiment, the free length 110 is about mm and the groove width 112 is about 0.3 mm on a 1.45 mm diameter guide wire. It should be noted that the guide wire, or K-wire, may include any diameter suitable for use as a guide wire or K-wire without departing from the scope of the invention. Additionally, gripper teeth 118 may be provided on the inner surfaces of the free ends 102, 104 to further engage the bone or tissue if needed. The embodiments illustrated in FIGS. 15C and 15D are similar to the embodiments of FIGS. 15A and 15B. In these embodiments, the radius 90 is moved closer to the distal ends 111,113 of the free ends 102, 104 and the included angle is increased to about 50 degrees to allow deployment within tighter spaces within a bone.

Referring to FIG. 16, an alternative embodiment of the present invention is illustrated. In this embodiment, the operative end 26 of the K-wire, or guide wire 10, includes a controllably deformable section 32 having a rocker member 120 mounted therein for limited rotation about a pin member 122. The rocker member 120 is preferably mounted to set within a groove 124 cut into the operative end 26 of the guide wire, or K-wire 10, so that the guide wire, or K-wire, may be inserted through a jamshidi and be retracted through a cannulated implant. A control rod, spring member or shape memory member (not shown) may be utilized to deploy and/or retract the rocker member.

Referring to FIG. 17, an alternative embodiment of the present invention is illustrated. In this embodiment, the operative end 26 of the K-wire, or guide wire 10, includes a controllably deformable section 32 comprising an expandable collet portion 126. The expandable collet portion includes a plurality of slits or grooves 128 between flexible fingers 127 to allow an expansion member 130 to be activated by temperature or a manually operated draw bar (not shown) to cause controlled expansion of the collet portion, thereby increasing the frontal area of the device. The collet portion is preferably formed from a spring or memory material so that the collet portion will return substantially to its original shape when the draw bar or temperature of the expansion member is returned substantially to its original condition for retraction of the device from the surgical site.

Referring to FIG. 18, an alternative embodiment of the present invention is illustrated. In this embodiment, the operative end 26 of the K-wire, or guide wire 10, includes a controllably deformable section 32 having a shape memory or spring core material (not shown) coated with a polymeric sheath 132.

Referring to FIG. 19, an alternative embodiment of the present invention is illustrated. In this embodiment, the operative end 26 of the K-wire, or guide wire 10, includes a controllably deformable section 32 having a plurality of vanes 134 constructed of shape memory or spring type material. In this embodiment, the manipulative end 26 of the guide wire, or K-wire, can be rotated in opposite directions about the longitudinal axis 116 to deploy or retract the vanes on the operative end 26. It should be noted that while the vanes are illustrated as being substantially straight along their length, they may be helical, curved or otherwise shaped to allow the desired deployment and retraction without departing from the scope of the invention.

Referring to FIG. 20, an alternative embodiment of the present invention is illustrated. In this embodiment, the operative end 26 of the K-wire, or guide wire 10, includes a controllably deformable section 32 having at least one, and more preferably two helically wound wire type members 136 attached at a distal end to a central core member 138. In this embodiment, the helical wire members may be constructed of a metal material sufficiently rigid to allow the guide wire or K-wire to be rotated, via the manipulative end, in a first direction into engagement within the bone and rotated in an opposite direction, via the manipulative end, to allow for the device to be removed from the bone.

Referring to FIG. 21, an alternative embodiment of the present invention is illustrated. In this embodiment, the operative end of the K-wire, or guide wire 10, includes a controllably deformable section 32 having four bar linkage 140 connected at one corner pin 142. A draw bar or cable (not shown) may be utilized to controllably expand and contract the four bar linkage to engage and release the bone.

Figure 14:
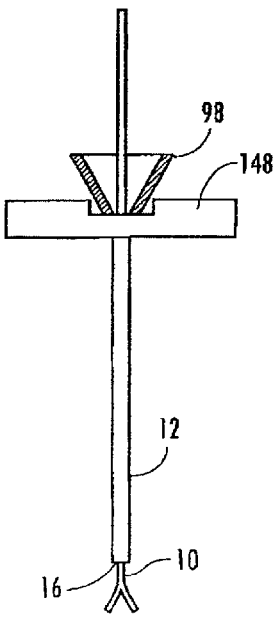
FIG. 14 is a view of one embodiment of the present invention extending through the cannula portion of a jamshidi needle.
Figure 24:
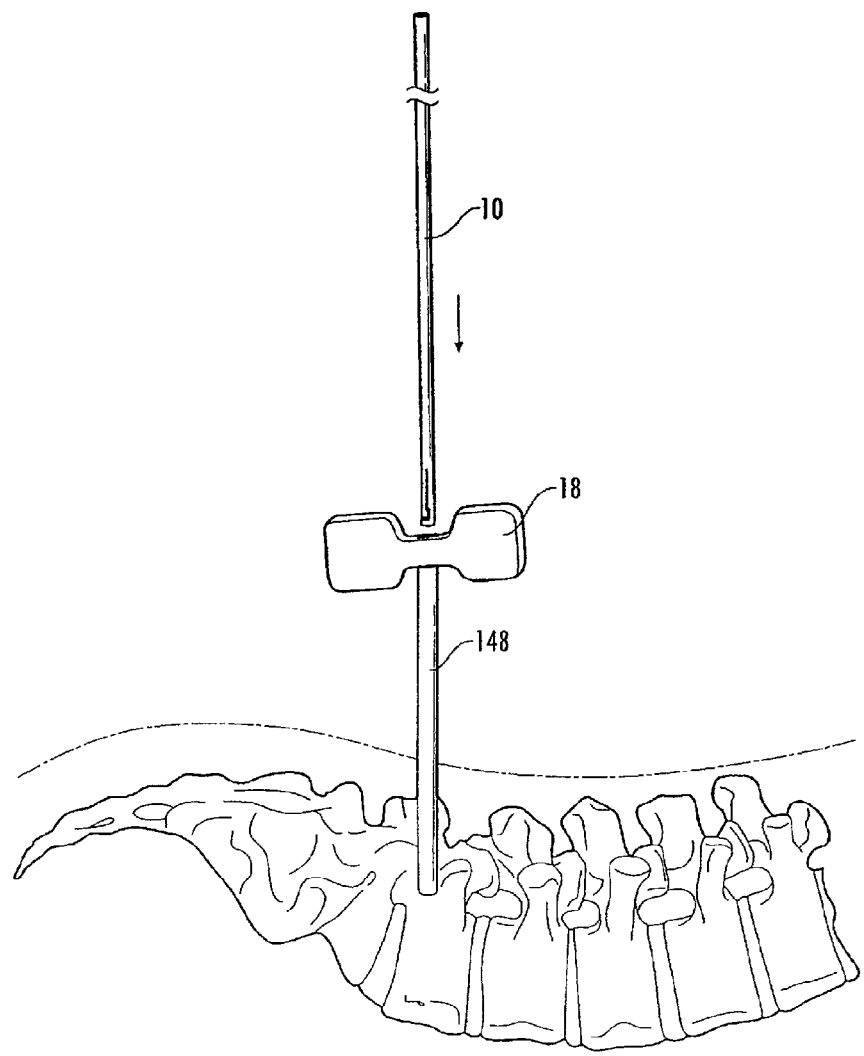
FIG. 24 is a partial side view illustrating the insertion of the K-wire, or guide wire, of the instant invention into the through bore within the jamshidi.
Figure 25:
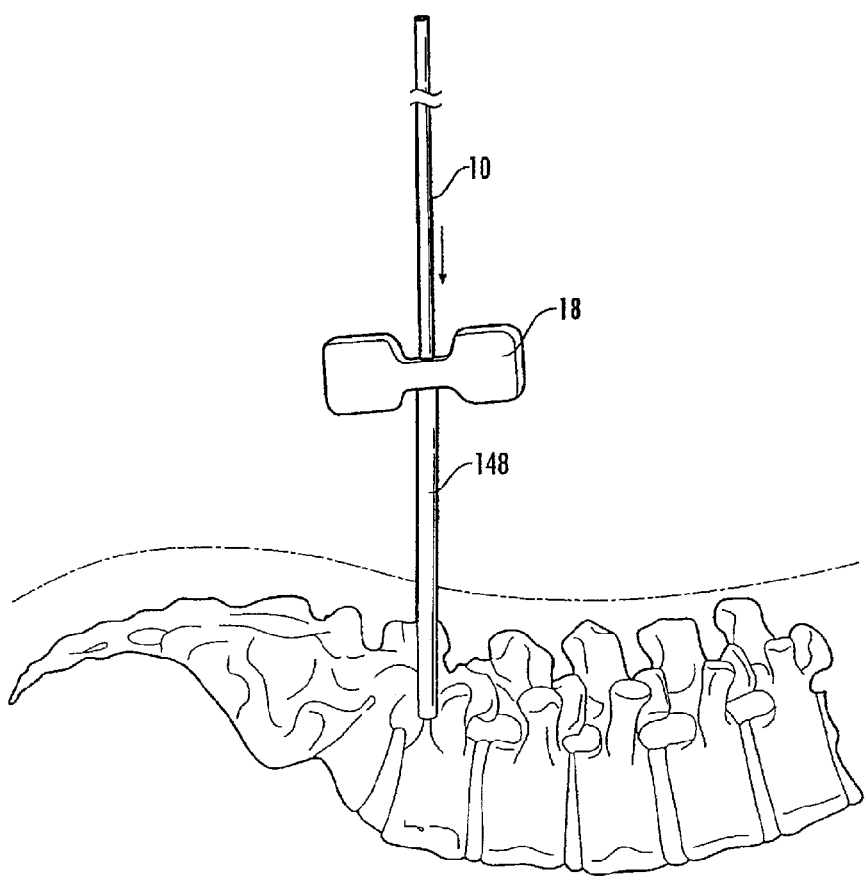
FIG. 25 is a partial side view illustrating the K-wire, or guide wire, emerging from the distal end of the jamshidi into the bone and deploying.
Figure 26:
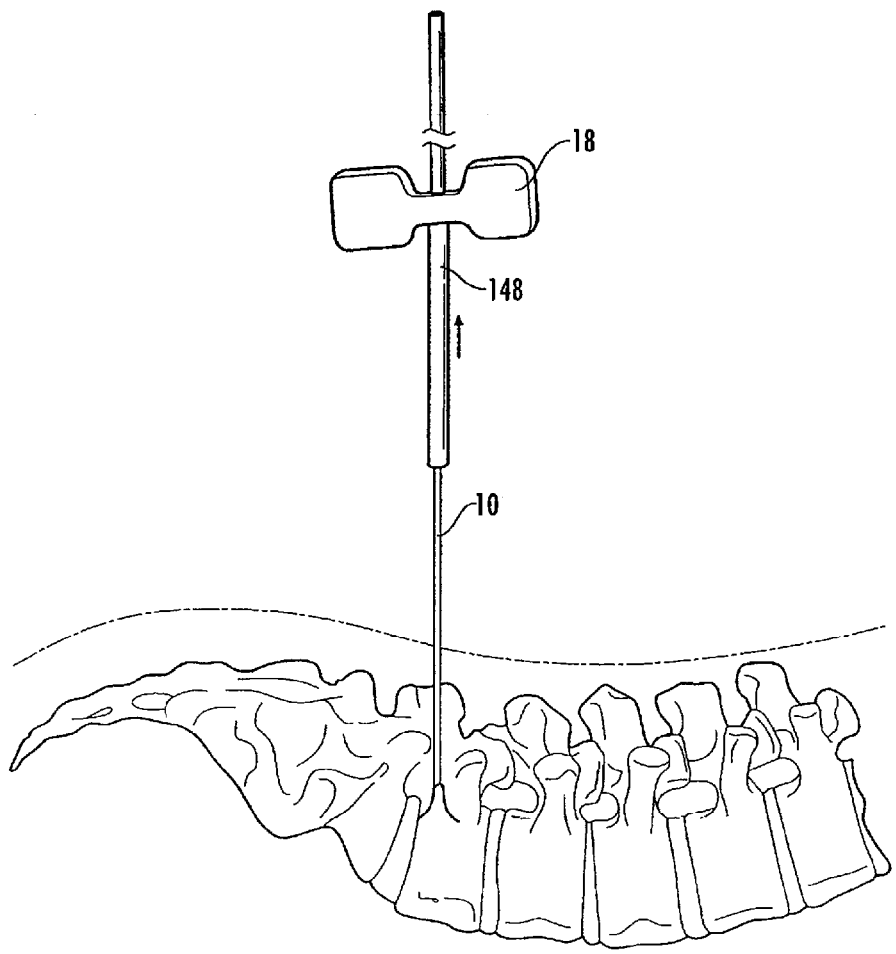
FIG. 26 is a partial side view illustrating the removal of the jamshidi and leaving the K-wire, or guide wire, in place within the bone in a deployed position.

The present invention also includes a method of conducting a medical procedure using a K-wire, or guide wire, as illustrated in FIG. 14. A surgeon or other medical personnel places a surgical tool such as a jamshidi 12 at the surgical site. The initial surgical tool preferably has a guiding through bore opening at the distal tool end such as that described above for a jamshidi needle 12. The jamshidi 12 is tapped or pressed into the bone at the desired angle as illustrated in FIG. 22. The needle portion of the jamshidi is then removed from the through bore as illustrated in FIG. 23 and a K-wire, or guide wire 10, is guided to the site by passing the K-wire, or guide wire, through the through bore 16 until the operative end 26 extends beyond the open end of the through bore 16. See FIG. 24. The jamshidi may include a lead in funnel 98 to help the surgeon place the K-wire, or guide wire, into the Jamshidi needle. The operative end 26 of the K-wire, or guide wire, has at least a portion deformed after its exit from the through bore 16, such that the deformed portion presents a projected area greater than the cross sectional area of the K-wire, or guide wire, when in the through bore 16 as described above. See FIG. 25. The deformation can occur automatically, as by increasing the temperature of the operative end portion 26, when it includes a memory metal alloy. The deformation may also be induced by relieving stress induced into the operative end portion, as when the deformable portion is constructed of a spring material. The deformation may also be induced mechanically by the application of an axially directed force along the K-wire, or guide wire 10. After at least a portion of the surgery, the K-wire, or guide wire, can be removed as described above. The K-wire, or guide wire, is used to guide surgical tools and/or devices to the surgical site during the surgical procedure. Once the K-wire, or guide wire, has been inserted into the bone, the jamshidi needle can be withdrawn and a cannulated tap or other instrument can be slid down the K-wire, or guide wire, and inserted into the bone. When the tap reaches the expanded ends 82, 84 of the K-wire, it may stop its forward progress. Thus, this invention avoids the need for fluoroscopy to determine the position of the tap or other instrument in a bone.

Figure 27:
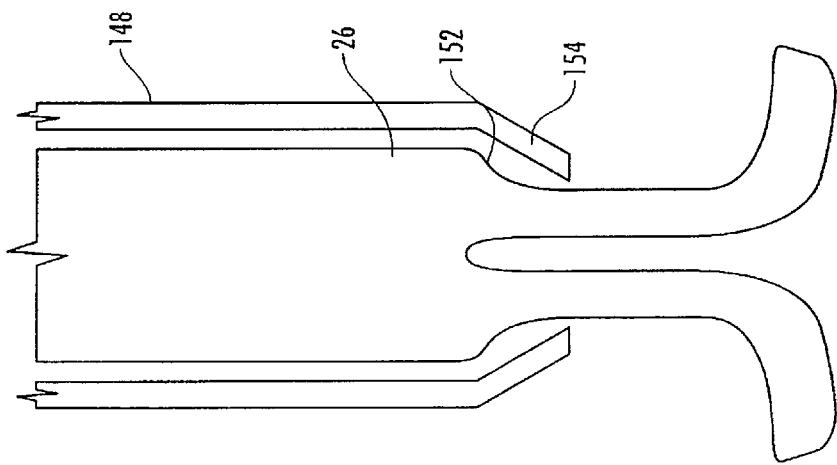
FIG. 27 is an enlarged end view of another embodiment of the present invention.

FIG. 27 illustrates a further embodiment of the present invention. A K-wire or guide wire 10 is similar to the K-wire or guide wires illustrated in FIGS. 15A-15D. The K-wire has an operative end portion 26 which includes a portion 152 which has been swaged down to a smaller diameter. The end of the K-wire 10 includes ends 102 and 104, similar to the ends of the embodiment of FIGS. 15A-15D. The ends 102 and 104 are formed from a material, such as a shape memory alloy, which permits the ends 102 and 104 to bend outwardly, as illustrated. The end 154 of tubular member 148 can be conically tapered, as illustrated. End 154 prevents the K-wire from completely exiting the tubular member 148. This is because the inner diameter of the tapered end 154 is smaller that the diameter of the K-wire before it has been swaged down to a smaller diameter. End 154 can also be provided with grooves or notches which enable the tube to readily cut or drill into a bone or similar material. Once the desired depth or location is achieved, the drills, taps, screws, etc. can be slid into place by sliding them down over tube 148.

Figure 28:
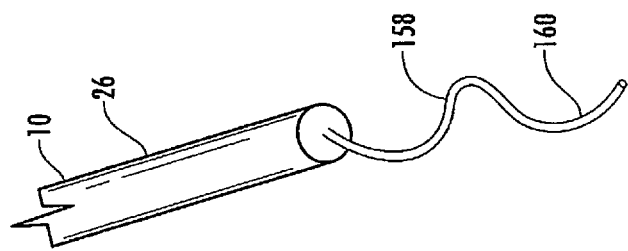
FIG. 28 is an enlarged perspective view of another embodiment of the present invention.

Referring to FIG. 28, an alternative embodiment of the present invention is illustrated. In this embodiment, the operative end 26 of the K-wire or guide wire 10, includes a controllably deformable section 158 having one helically wound wire type member 160 attached to the operative end 26 of the K-wire 10. In this embodiment, the helical wire 160 may be constructed of a metal material sufficiently rigid to allow the K-wire to be rotated, via the manipulative end, in a first direction into engagement with the bone and rotated in an opposite direction, via the manipulative end, to allow for the device to be removed from the bone.

It is to be understood that while certain forms of the invention are illustrated, it is not to be limited to the specific forms or arrangements herein described and shown.

It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A guide wire for the introduction of surgical implants and surgical instruments to a surgical site within a body, the guide wire comprising: a body having a manipulative end, a center portion and an operative end, said operative end portion comprising two equally sized deployable free ends which diverge from a common region of said body, each said free end having a first linear portion and a second portion which diverges from the longitudinal axis of said body at a bend, said bend positioned between said common region of said body and a distal end of said of free end, wherein each said bend is positioned at a predetermined location within said free end to provide a predetermined separation angle, wherein each said free end contains at least one bone or tissue engagement member includes a plurality of teeth provided on an inner surface of each free end.

2. The guide wire of claim 1 wherein said bend of each said free end is positioned closer to said distal end of said free end.

3. The guide wire of claim 1 wherein said bend of each said free end is positioned closer to said point where said free ends diverge from a common region of said body.

4. The guide wire of claim 1 wherein each said bend is positioned at a predetermined location within said free ends to provide an angle of at least 30 degrees.

5. The guide wire of claim 1 wherein each said bend is positioned at a predetermined location within said free ends to provide an angle of at least 50 degrees.

6. The guide wire of claim 1 wherein each said free end is constructed from a flexible material.

7. The guide wire of claim 6 wherein each said free end is constructed from a memory metal alloy.

8. The guide wire of claim 7 wherein said memory metal alloy is a super-elastic material.

9. The guide wire of claim 7 wherein the memory metal alloy includes Nitinol.

10. The guide wire of claim 1 wherein said each said deployable end is constructed from a memory metal alloy.

11. The guide wire of claim 1 wherein said each said deployable end is constructed of a resiliently deformable spring material.

12. The guide wire of claim 1 wherein said each said deployable end has a deformable portion made of a plastically deformable material.

13. The guide wire of claim 1 wherein each said free end is self deployable.

* * * * *